United States Patent
Shtram et al.

(10) Patent No.: US 11,185,631 B2
(45) Date of Patent: Nov. 30, 2021

(54) ACCURATE FLOW RATE ADJUSTMENT FOR IV PUMP

(71) Applicants: Lior Shtram, Tel Aviv (IL); Eyal Barmaimon, Haifa (IL); Shai Finkman, Haifa (IL); Ronny Bellan, Nazareth (IL); Michael Zeltsburg, Naharia (IL)

(72) Inventors: Lior Shtram, Tel Aviv (IL); Eyal Barmaimon, Haifa (IL); Shai Finkman, Haifa (IL); Ronny Bellan, Nazareth (IL); Michael Zeltsburg, Naharia (IL)

(73) Assignee: FLEX LTD., Singapore (SG)

( * ) Notice: Subject to any disclaimer, the term of this patent is extended or adjusted under 35 U.S.C. 154(b) by 41 days.

(21) Appl. No.: 15/961,104

(22) Filed: Apr. 24, 2018

(65) Prior Publication Data
US 2019/0015589 A1    Jan. 17, 2019

Related U.S. Application Data

(60) Provisional application No. 62/532,163, filed on Jul. 13, 2017.

(51) Int. Cl.
| A61M 5/168 | (2006.01) |
| A61M 5/142 | (2006.01) |
| A61M 5/172 | (2006.01) |

(52) U.S. Cl.
CPC .... *A61M 5/16895* (2013.01); *A61M 5/14228* (2013.01); *A61M 5/172* (2013.01);
(Continued)

(58) Field of Classification Search
CPC .......... A61M 5/16895; A61M 5/14228; A61M 5/16845; A61M 5/172; A61M 5/1723;
(Continued)

(56) References Cited

U.S. PATENT DOCUMENTS

| 4,457,750 A | 7/1984 | Hill |
| 4,954,046 A | 9/1990 | Irvin et al. |

(Continued)

FOREIGN PATENT DOCUMENTS

| CN | 102631727 A | 8/2012 |
| CN | 104014009 A | 9/2014 |

(Continued)

*Primary Examiner* — Tiffany Legette
(74) *Attorney, Agent, or Firm* — Volpe Koenig

(57) ABSTRACT

A device and method for measuring an IV pump infusion system flow comprises a fluid source configured to store medicinal fluid and a weight sensing mechanism comprising a weight sensor and microprocessor. The weight sensing mechanism is configured to detect the weight of the fluid source as the medicinal fluid leaves the fluid source. The device in the infusion system administers medicinal fluid using a set flow rate for the IV pump input into the control unit prior to infusion, measures the change in mass of the fluid source containing medicinal fluid as fluid exits the source, calculates the flow rate based on the change in mass over time, compares the calculations with a set flow rate, and adjusts the IV pump and flow rate based on the compared deviations, for improved delivery accuracy. This configuration may also prevent patient harm and medicine waste.

18 Claims, 4 Drawing Sheets

(52) U.S. Cl.
CPC ............... *A61M 2205/3334* (2013.01); *A61M 2205/3365* (2013.01); *A61M 2205/3393* (2013.01); *A61M 2205/50* (2013.01); *A61M 2205/502* (2013.01); *A61M 2205/52* (2013.01); *A61M 2209/084* (2013.01)

(58) Field of Classification Search
CPC .. A61M 2205/3393; A61M 2205/3334; A61M 2205/3365; A61M 2205/50; A61M 2205/502; A61M 2205/52; A61M 2209/084
See application file for complete search history.

(56) References Cited

U.S. PATENT DOCUMENTS

| | | |
|---|---|---|
| 8,882,701 B2 | 11/2014 | DeBelser et al. |
| 2005/0145010 A1* | 7/2005 | Vanderveen ...... A61M 5/16827 73/1.57 |
| 2005/0230575 A1* | 10/2005 | Zelenski ............. A61G 7/0503 248/176.1 |
| 2005/0238497 A1 | 10/2005 | Holst et al. |
| 2008/0171966 A1* | 7/2008 | Rudko ................ A61M 5/1723 604/29 |
| 2008/0177222 A1* | 7/2008 | Roger .................. A61M 1/341 604/29 |
| 2008/0221512 A1* | 9/2008 | Da Silva .................. A61B 5/20 604/65 |
| 2010/0192686 A1* | 8/2010 | Kamen ................... A61M 1/16 73/290 R |
| 2014/0228755 A1 | 8/2014 | Darrah et al. |
| 2014/0345609 A1* | 11/2014 | Whitcher .......... A61M 16/0677 128/202.26 |
| 2015/0133888 A1* | 5/2015 | Ali .......................... G16H 20/17 604/503 |
| 2016/0287785 A1* | 10/2016 | Isaacson ........... A61M 5/16881 |
| 2016/0370911 A1* | 12/2016 | Tanenbaum ........ A61M 1/1601 |

FOREIGN PATENT DOCUMENTS

| | | |
|---|---|---|
| EP | 2 564 885 A1 | 3/2013 |
| KR | 20160053332 A | 5/2016 |
| WO | 2016/160527 A1 | 10/2016 |

* cited by examiner

ACCURATE FLOW RATE ADJUSTMENT FOR IV PUMP

CROSS REFERENCE TO RELATED APPLICATIONS

This application claims the benefit of U.S. provisional application No. 62/532,163 filed Jul. 13, 2017, which is incorporated by reference as if fully set forth.

SUMMARY

A device and method for measuring and adjusting an IV pump infusion system flow comprising a weight sensing mechanism that includes a weight sensor and microprocessor, and a fluid source. The weight sensing mechanism is configured to measure the change in mass of the fluid source containing the medicinal fluid over a time interval, as the medicinal fluid exits the fluid source and enters the infusion system during infusion. The device in the infusion system is configured to calculate the flow rate of the medicinal fluid during infusion based on the measured change in mass of the fluid source containing the medicinal fluid over time, compare the calculated flow rate with a set flow rate of the IV pump input into the control unit prior to infusion, and adjust the IV pump and flow rate based on the compared deviation for more precise medicine administration.

BRIEF DESCRIPTION OF THE DRAWINGS

The present invention is illustrated by way of example, and not by way of limitation, in the figures of the accompanying drawings in which.

DETAILED DESCRIPTION OF THE PREFERRED EMBODIMENTS

Figure 1:
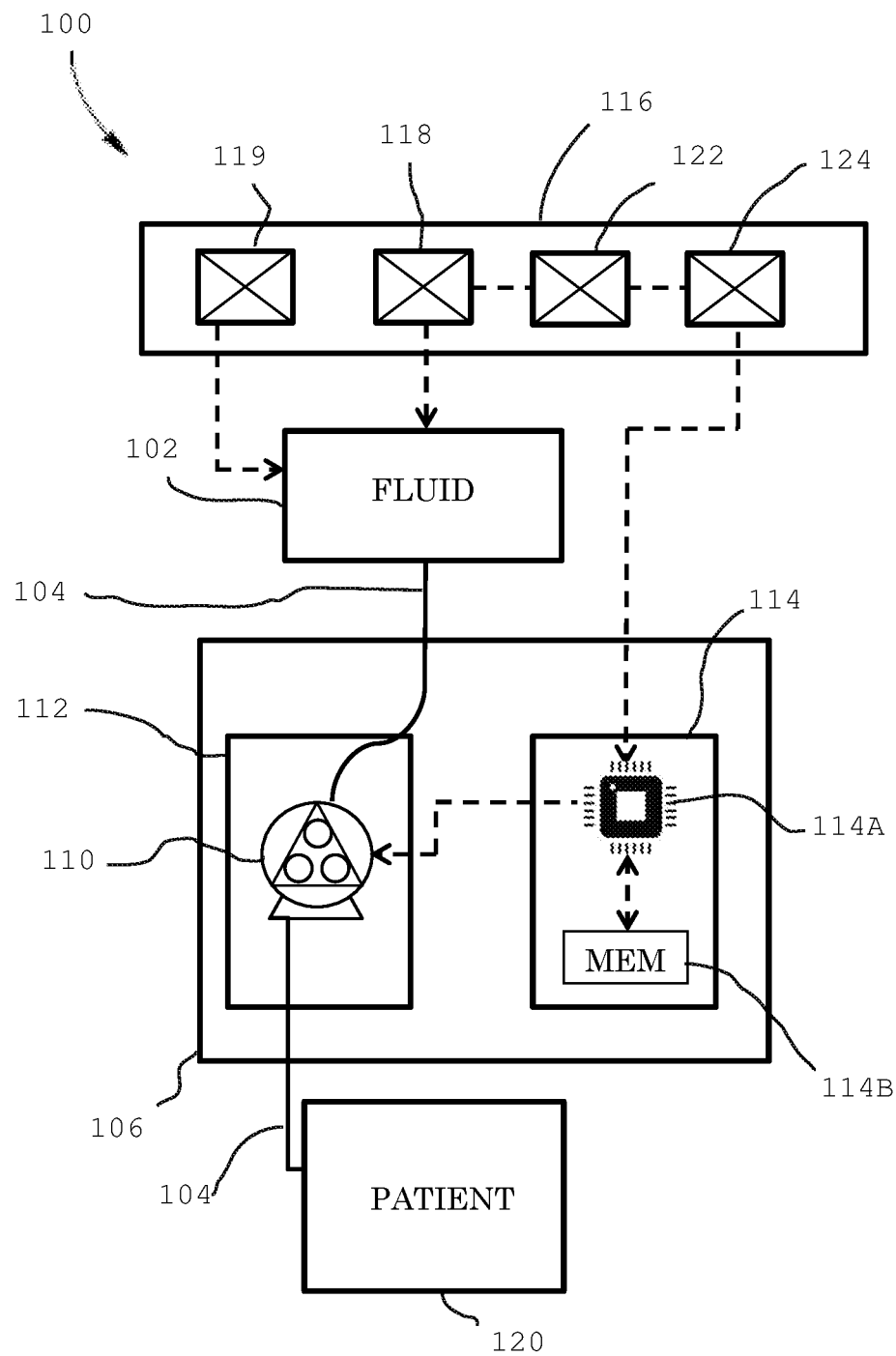
FIG. 1 is a schematic block diagram of an IV infusion pump with a flow and volume measurement system.

Intravenous ("IV") infusion is a popular type of therapy that efficiently delivers liquid substances to a patient directly through a vein. IV infusion is necessary for the treatment of a variety of broad ranging diseases, conditions, and symptoms. The infusion system, delivery method, and flow and dosage details are therefore imperative in determining effective drug administration and therapy.

IV pumps play a crucial role in delivering fluids and complex doses of medications to patients in a wide range of care settings. Currently, medications and pharmaceutical drugs administered through the IV pump attempt to infuse at a smooth and continuous flow rate that is input into the infusion system prior to infusion. Delivery accuracies, however, greatly vary. IV pump inaccuracies typically result from the disposable infusion systems used.

One reason for inaccuracies in infusion systems is because the systems have a common tube inner diameter tolerance of ±0.05 mm. This variance of inner diameter tolerance causes the volume of substance being delivered through the IV infusion system to fluctuate. As a result of such fluctuation, drug delivery to a patient may not be precise and could result in harm to the patient or wasting of the medication or substance to be administered.

Another reason for inaccuracies in infusion systems is because of current flow rate measurement mechanisms. Currently, there is no direct flow measurement of the pharmaceutical drug in the infusion system. The delivered dose is instead measured based on a calculation that correlates the motor rotation speed tube diameter and amount of pharmaceutical drug. This calculation, however, may be problematic if the drug in the bag was finished due to pump inaccuracies.

To combat some of these inaccuracies, current IV systems are equipped with pressure sensors to monitor the change in pressure inside the tubing. One of the pressure sensors is typically placed between the pump and the patient, while the other is placed between the fluid source and pump. The pressure sensors are used to measure the pressure change of the tubing if the flow rate changes (due to depletion of the drug, kinked tubing, etc.). This configuration, however, still provides problematic and inaccurate results. The rate of change in pressure depends on the flow rate of the infusion system. As a result, it may take a longer period of time before the pressure sensors detect the initial change in pressure. As a result, the infusion pump continues its set speed without taking into effect the change in flow rate between the time the flow rate changes and the time the changed flow rate is detected. This configuration therefore leads to inaccuracies during infusion.

It would therefore be beneficial to offer an IV infusion flow and volume measurement system and method that calculates the flow rate of a medicinal substance and adjusts the infusion system according to any deviations found, to help improve substance-delivery accuracy.

FIG. 1 is a schematic block diagram of an IV infusion pump with a flow and volume measurement system 100 in accordance with the teachings herein. The flow and volume measurement system 100 comprises a fluid source 102; IV tubing 104; an infusion system 106 that includes an IV pump 110, a drive unit 112, and a control unit 114; and a weight sensing mechanism 116.

In the present embodiment as described hereinafter, the flow and volume measurement system 100 may be used in IV infusion therapies, and for purposes of explanation, the flow and volume measurement system 100 will be described with reference to IV infusion. However, those of skill in the art would realize that in other embodiments, the flow and volume measurement system 100 may be used to perform other therapeutic or diagnostic procedures. During IV infusion, a practitioner may use an infusion system and an IV pump to deliver a precise amount of medicinal fluid into a patient's vein over a controlled period of time. Linear peristaltic pumps are typically used in order to maintain sterilization of the IV infusion system. These pumps require a peristaltic apparatus that occludes a resilient IV tube through which the IV fluid is pumped. The tubing is compressed against a stationary plate and the compression and decompression regulate the desired flow. When the tubing occludes, the tubing forces the fluid to go through the patient's vessel at a pre-selected rate.

Current manufactured tubing for linear peristaltic IV pumps, however, vary slightly in inner diameter and outer diameter size. For example, this tubing may have an inner diameter ("ID") tolerance of ±0.05 mm or more. This tolerance effect ultimately impacts the volume inside the tubing. For example, the nominal volume inside an IV tube is currently calculated using the following equation:

$$v_{nom} = \pi \times \frac{ID^2}{4} \times \Delta l \qquad \text{Equation (1)}$$

where $\Delta l$ is a specified width of the peristaltic pump finger. In contrast, the maximum volume inside the IV tube, taking into consideration the ±0.05 mm tolerance, is calculated as follows:

$$v_{max} = \pi \times \frac{(ID + 0.05)^2}{4} \times \Delta l \qquad \text{Equation (2)}$$

As a result, the current tolerance effect of IV tubing inner diameters provides approximately a 3.5% change (calculated for an ID of 3 mm, which is a common inner diameter in IV tubing) in volume inside the tubing. Having a tube volume deviation of ±3.5% makes it difficult to effectively administer the precise amount of medicinal fluid over a specific time to a patient, since the volume inside the tube varies. The inability to measure the exact flow rate of fluid inside the tubing without expensive in-line products also makes it difficult to combat the variance in administration due to tube volume deviation. As a result, the patient may be administered more or less medicine than the required dosage, which could ultimately harm the patient. Administering an excess dosage of medicinal fluid also unnecessarily wastes expensive medicine.

In addition, there is no direct flow measurement of the pharmaceutical drug in the infusion system, without the use of expensive in-line products. As a result, the drug depletion may not be monitored in time causing the pump to continue pumping without any means to sense that there is no drug left for delivery.

Returning to FIG. 1, in the present embodiment, the flow and volume measurement system 100 measures the flow rate and the dispensed volume of medicinal fluid during infusion using the weight sensing mechanism 116, and then transmits the data to the infusion system 106, which compares the calculated flow rate with an input flow rate in order to adjust infusion for more accurate medicine delivery. The flow rate is calculated by measuring the change in mass over a time interval of the fluid source 102 storing medicinal fluid as the medicinal fluid enters the peristaltic IV pump 110. This change in mass is measured by the weight sensing mechanism 116. The fluid source 102 hangs from the weight sensing mechanism 116. The weight sensing mechanism 116 must therefore include a weight sensor 118 to detect the change in mass and measure the mass of the fluid source 102 containing the medicinal fluid both prior to and during infusion. The weight sensing mechanism 116 further includes an accelerometer 119 to verify that the fluid source 102 is not moving while the measuring is taking place, a microprocessor 122 to help determine the flow and volume, and a communication unit 124. The microprocessor 122 may communicate data to the communication unit 124, and the communication unit 124 may subsequently communicate this data to the microprocessor 114A of the control unit 114.

In one embodiment, the weight sensor 118 may be a strain gauge that measures the change in strain from the fluid source 102 containing medicinal fluid as a change in electrical resistance. In other embodiments, the weight sensor 118 may include any type of weight sensing scale. In the embodiment set forth in the drawings and as described hereinafter, the fluid source 102 is an IV bag, but that is just by way of example. In other embodiments, the fluid source 102 may be any sterilized container able to store the medicinal fluid.

When infusion begins, the medicinal fluid stored in the fluid source 102 flows through the IV tubing 104 and to a patient 120. The control unit 114 may begin infusion by communicating with the drive unit 112 to operate the IV pump 110. The control unit 114 may comprise a microprocessor 114A and a memory 114B. In other embodiments, the control unit 114 may use other types of logic devices for operating the drive unit 112, such as a hardwired logic control, an application-specific integrated circuit, etc. In one embodiment, the drive unit 112 may comprise an electrical motor to drive the IV pump 110.

In the present embodiment, the IV pump 110 is a standard peristaltic pump. Accordingly, the IV tubing 104 is a standard manufactured tubing commonly used with peristaltic IV pumps, and thus has an ID tolerance of approximately ±0.05 mm.

The IV pump 110 operates at a rotational speed that is set prior to infusion. As the medicinal fluid flows out of the fluid source 102 through the IV tubing 104 during infusion, the mass of the fluid source 102 containing the medicinal fluid decreases. The weight sensing mechanism 116 measures the change in mass of the fluid source 102 over a time period.

In one embodiment, the weight sensing mechanism 116 then calculates the actual flow rate of the medicinal fluid using the equation:

$$\text{Flow rate} = \frac{1}{\Delta t} \times \frac{\Delta m}{\rho} \qquad \text{Equation (3)}$$

Where $\Delta t$ is the change in time between a first and second time interval as the medicinal fluid leaves the fluid source 102, and $\Delta m$ is the change in mass between the first and second time interval. The weight sensing mechanism 116 then displays the data on an internal display (not depicted). In another embodiment, the weight sensing mechanism 116 transmits the raw data $\Delta m$ and $\Delta t$ to the control unit 114. The control unit 114 then calculates the actual flow rate of the medicinal fluid using Equation (3).

In one embodiment, the weight sensing mechanism 116 may be communicatively connected to the control unit 114 through electrical wiring. In another embodiment, the weight sensing mechanism 116 may be communicatively connected to the control unit 114 wirelessly. The control unit 114 may store the calculated flow rate values of the medicinal fluid leaving the fluid source 102 in the memory 114B. The control unit 114 may calculate the volume of the medicinal fluid as it flows in the flow and volume measurement system 100. The control unit 114 may compare the calculated volume of the medicinal fluid with the set speed and flow rate of the IV pump 110 prior to infusion. If the calculated flow rate of the medicinal fluid deviates from the pre-set flow rate from the IV pump 110, the control unit 114 may communicate with the drive unit 112 and the IV pump 110 to adjust the IV pump 110 to a rotational speed to achieve an accurate flow rate delivery. In one embodiment, the IV pump 110 may be communicatively connected to the control unit 114 through electrical wiring. The control unit 114 and the drive unit 112 may adjust the IV pump 110 via the motor. The control unit 114 and drive unit 112 therefore adjusts the volume and flow rate based on the speed of the IV pump 110 to achieve the precise and required medicine delivery to the patient 120.

The control unit 114 and the drive unit 112 may also adjust the period of time for medicine delivery to the patient to compensate for the adjusted volume and flow rate of the IV pump 110. If the calculated flow rate of the medicinal fluid is greater than the pre-set flow rate, the control unit 114 and the drive unit 112 may decrease the period of time for drug delivery as the IV pump 110 is adjusted to achieve the desired flow rate. If the calculated flow rate of the medicinal fluid is lower than the pre-set flow rate, the control unit 114 and the drive unit 112 may extend the period of time for drug delivery as the IV pump 110 is adjusted to achieve the desired flow rate. As a result, the medicinal fluid is delivered into the patient 120 with improved volume accuracy and flow rate in a manner that does not harm the patient 120 when the flow rate is adjusted.

Figure 2:
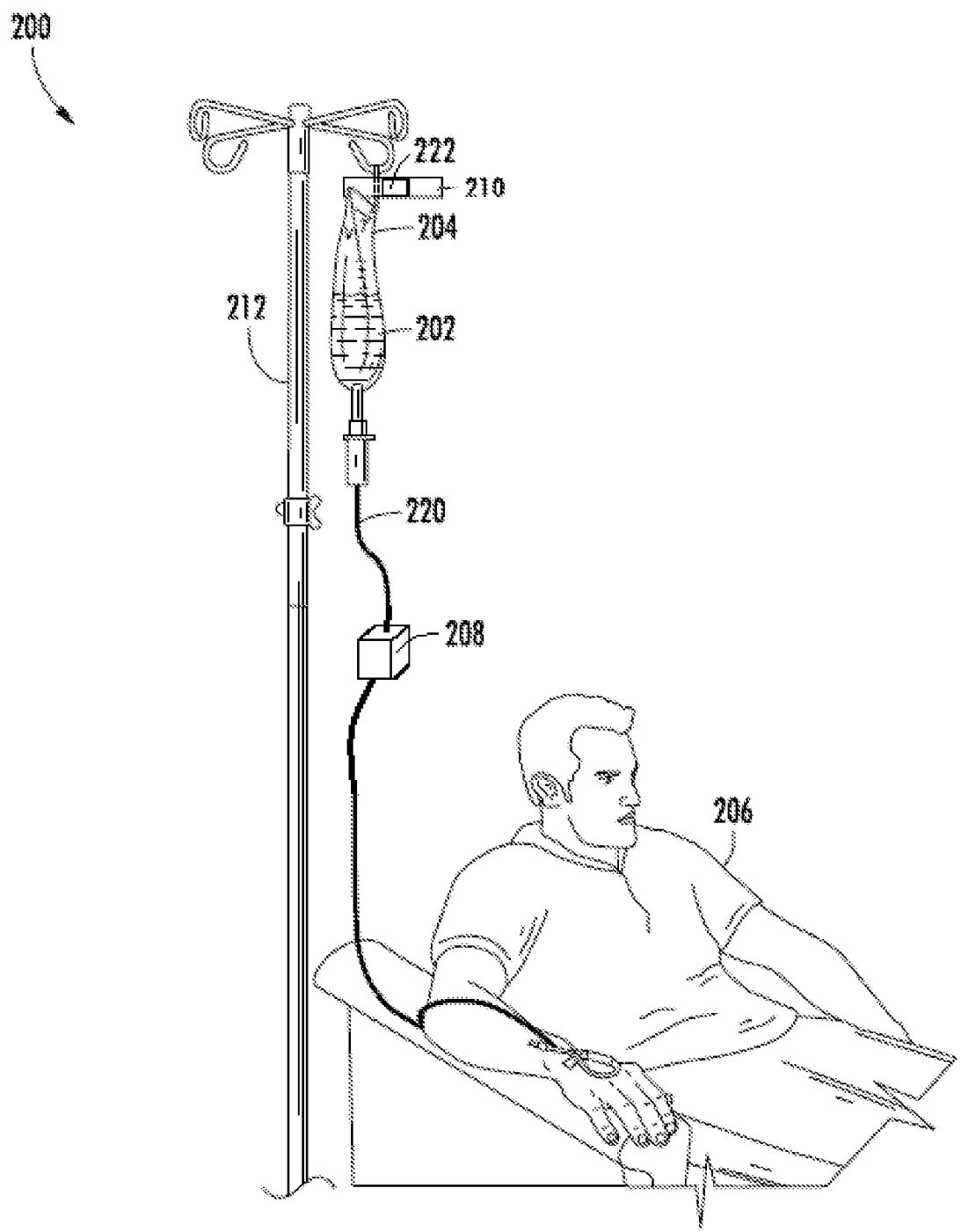
FIG. 2 is a pictorial illustration of infusion of medicinal fluid to a patient based on gravity with a flow and volume measurement system.

FIG. 2 is a pictorial illustration of infusion of medicinal fluid to a patient based on gravity with a flow and volume measurement system. In the embodiment set forth in the drawings and as described hereinafter, the flow and volume measurement system 200 operates by gravity feed. Medicinal fluid 202 is administered from a fluid source 204 to a patient 206 through the IV tubing 220 and a manual valve 208, which can be adjusted by an operator. When the medicinal fluid 202 is administered, the flow of the medicinal fluid 202 through the IV tubing 220 is measured using a weight sensing mechanism 210 and displayed on the display unit 222. The fluid source 204 hangs directly from the base of the weight sensing mechanism 210 such that the weight sensing mechanism 210 is able to accurately measure the mass of the fluid source 204 containing the medicinal fluid 202. The fluid source 204, and therefore the weight sensing mechanism 210, must be fixed to a structure at a height that is higher than an administration location in the patient 206. This configuration allows the fluid source 204 to hang directly from the weight sensing mechanism 210 for accurate weight measurement.

In the present embodiment, the weight sensing mechanism 210 is fixed to an IV pole 212. In another embodiment, the weight sensing mechanism 210 may be fixed to any structure that allows the weight sensing mechanism 210 to accurately measure the change in mass of the medicinal fluid 202 of the fluid source 204.

Figure 3:
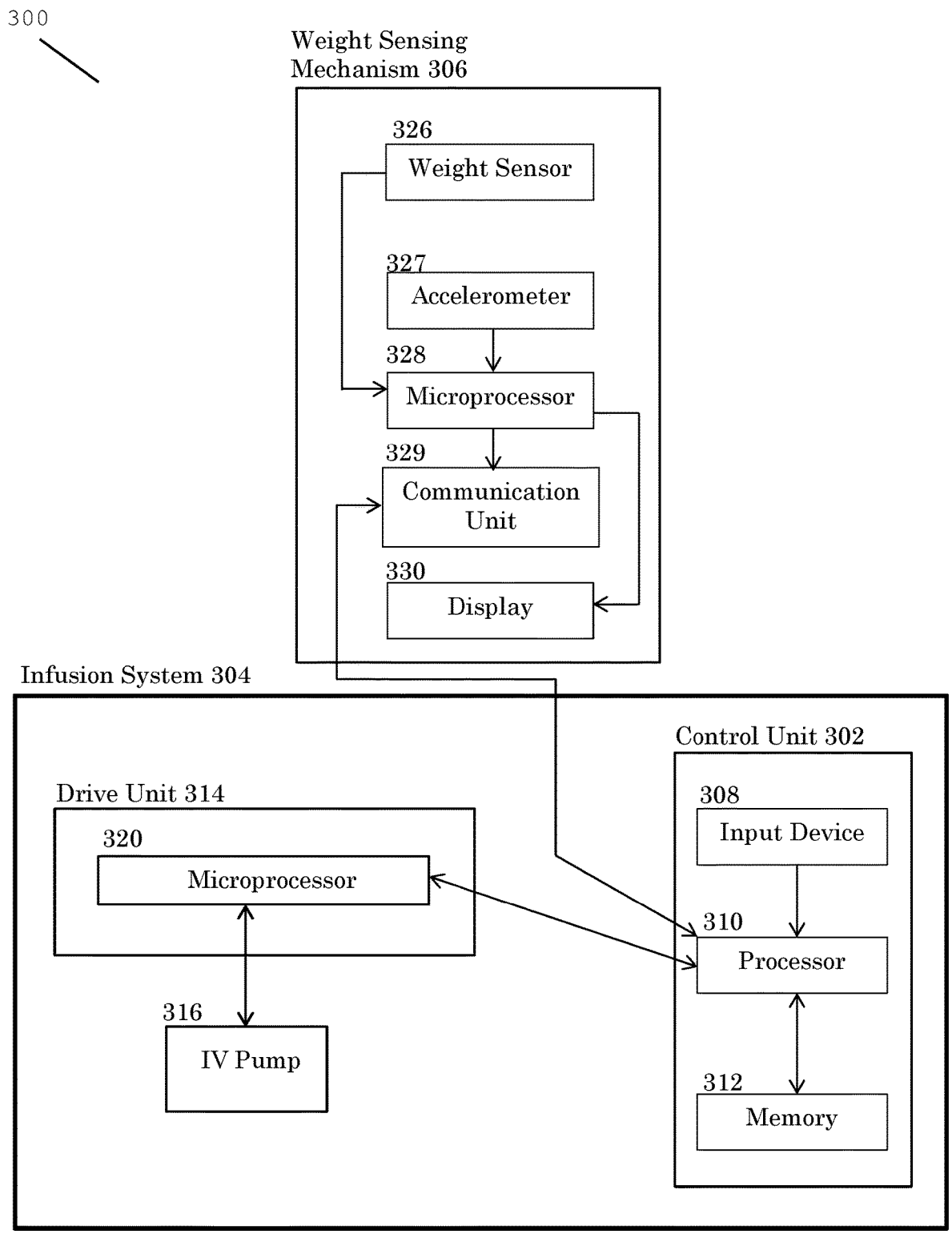
FIG. 3 is a block diagram of electrical components of an infusion flow and volume measurement system.

FIG. 3 is a block diagram of electrical components of an IV infusion flow and volume measurement system 300. In one embodiment, the flow and volume measurement system 300 comprises a weight sensing mechanism 306 that includes a weight sensor 326, an accelerometer 327, a microprocessor 328, a communication unit 329, and a display 330. The weight sensing mechanism 306 includes the accelerometer 327 for improving weight measurement accuracy when the fluid source is not steady. Once the flow and volume is determined by the weight sensor 326 and the microprocessor 328, the information may be transmitted using the communication unit 329 or may be displayed on the embedded display 330 so that an operator may use the manual valve (not depicted) to adjust the flow and the period of time for infusion.

In another embodiment, the flow and volume measurement system 300 comprises a separate infusion system 304 and a weight sensing mechanism 306. However, it should be understood that other configurations are possible, including a combination of the control unit 302, the infusion system 304, and the weight sensing mechanism 306.

In the present embodiment, the infusion system 304 includes a control unit 302. The control unit 302 includes an input device 308, a processor 310, and a memory 312. The input device 308 and the memory 312 are coupled to the processor 310. The infusion system 304 further includes a drive unit 314, and an IV pump 316. The drive unit 314 comprises a microprocessor 320.

The processor 310 is coupled to the infusion system 304 via the microprocessor 320 in the drive unit 314. The processor 310 is also coupled to the weight sensing mechanism 306 via the communication unit 329. It should be noted that although the embodiment set forth in the drawings and as described hereinafter shows three different processors used in the flow and volume measurement system 300, those of skill in the art would appreciate that the processors could be combined into one.

Prior to infusion, a set rotational speed and equivalent flow rate for the IV pump 316 is input into the control unit 302 using the input device 308. The input device then communicates the input to the processor 310. The processor 310 may comprise a general-purpose computer, with suitable front end and interface circuits for receiving signals from the input device 308, the drive unit 314, and the weight sensing mechanism 306. The processor 310 also controls the drive unit 314 to operate the IV pump 316 and thus control the fluid flow of the medicinal fluid in the flow and volume measurement system 300. These inputs and calculated values may be stored in the memory 312 of the control unit 302 for comparison with the calculated flow rate of the medicinal fluid when measured by the weight sensing mechanism 306 during infusion.

Initiation of infusion is also input into the input device 308. The input device 308 then communicates the initiation input to the processor 310. The processor 310 communicates with the microprocessor 320 of the drive unit 314. The drive unit 314 and microprocessor 320 control the IV pump 316 and allow medicinal fluid to flow out of a fluid source to a patient for administration.

As medicinal fluid flows out of the fluid source, the weight sensor 326 of the weight sensing mechanism 306 detects a change in mass of the fluid source and begins to measure the decreasing mass over time. The weight sensor 326 then sends the mass and time data to the microprocessor 328. The microprocessor 328 may communicate the mass and time data to the communication unit 329, or display the information on the display 330 for the operator. The communication unit 329 may also communicate this data to the processor 310 of the control unit 302. The processor 310 may then use the data to calculate the flow rate of the medicinal fluid in the system 300 as well as the volume of the medicinal fluid flowing through the flow and volume measurement system 300 and store the data in the memory 312.

Figure 4:
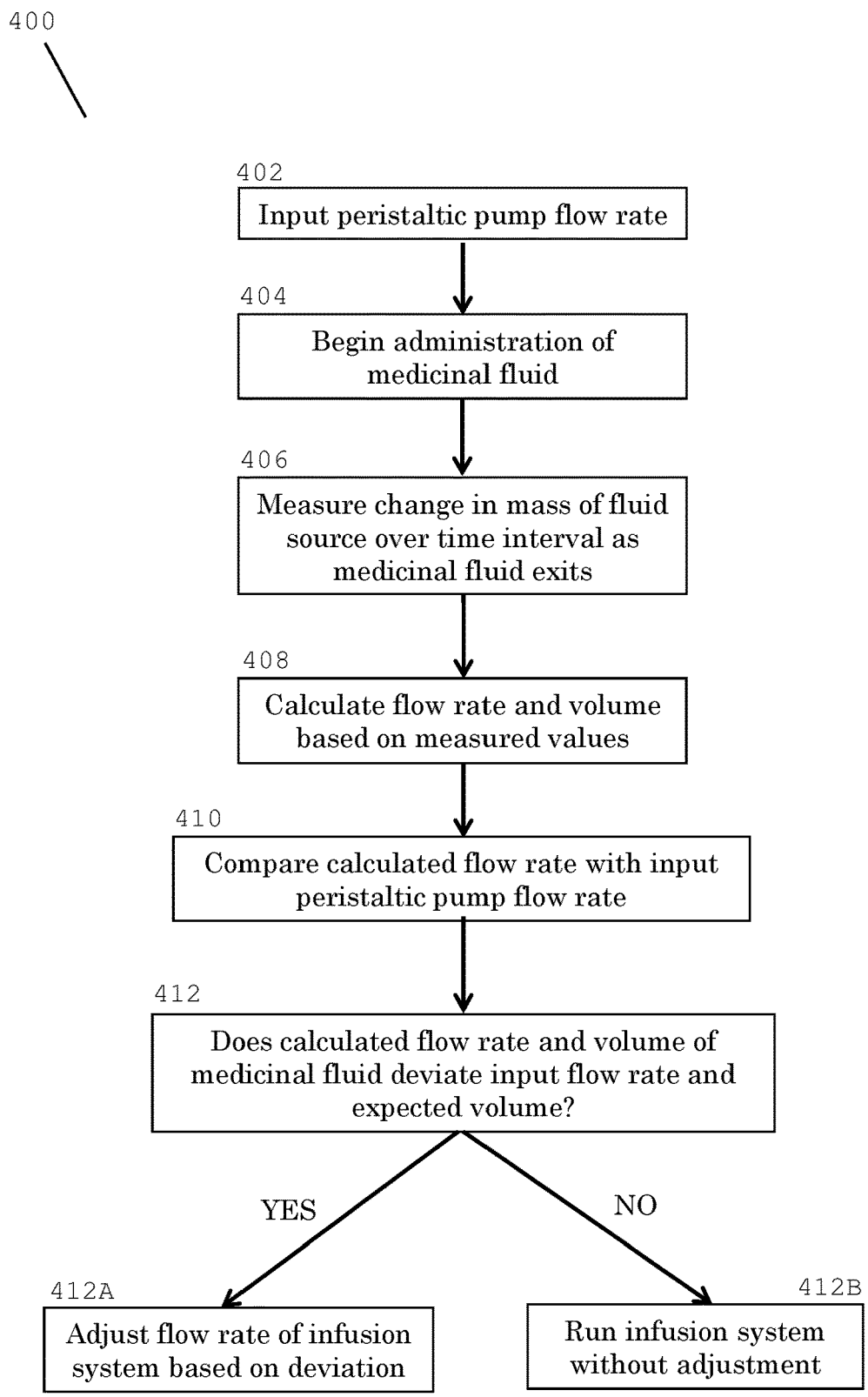
FIG. 4 is a flow diagram of a method of flow and volume measurement for an IV infusion system.

FIG. 4 is a flow diagram of a method 400 of flow rate adjustment for an IV infusion system. Once the system is primed, the rotational speed and equivalent flow rate of the IV pump is input into the infusion system (402). The medicinal fluid is then released from a fluid source and administration of the medicinal fluid begins (404). A weight sensing mechanism measures the change in mass of the fluid source over a time interval as medicinal fluid is released during administration (406).

The flow rate and volume of the medicinal fluid in the chamber is calculated based on the measured change of mass over the specified time interval (408). The calculated flow rate is compared to the input flow rate for the IV pump (410, 412). If the calculated volume and flow rate deviates from the set flow rate prior to infusion, the flow rate is adjusted to meet the proper administration requirements (412A). The period of time for medicine administration may also be adjusted to compensate for the adjusted flow rate. If the calculated volume and flow rate does not deviate from the set flow rate prior to infusion, the flow rate is not adjusted and the infusion system continues to run without adjustment (412B). This configuration provides more accurate required dosage of medicine over a more precise duration based on known deviations of volume of the medicinal fluid being administered due to IV tubing tolerance.

Having thus described the presently preferred embodiments in detail, it is to be appreciated and will be apparent to those skilled in the art that many physical changes, only a few of which are exemplified in the detailed description of the invention, could be made without altering the inventive concepts and principles embodied therein. It is also to be appreciated that numerous embodiments incorporating only part of the preferred embodiment are possible which do not alter, with respect to those parts, the inventive concepts and principles embodied therein. The present embodiments and optional configurations are therefore to be considered in all respects as exemplary and/or illustrative and not restrictive, the scope of the invention being indicated by the appended claims rather than by the foregoing description, and all alternate embodiments and changes to this embodiment which come within the meaning and range of equivalency of said claims are therefore to be embraced therein.

The invention claimed is:

1. A measurement device for an IV infusion system, comprising:
   a fluid source configured to store medicinal fluid; and
   a weight sensing mechanism comprising a weight sensor and a microprocessor;
   wherein the weight sensor is configured to detect a weight of the fluid source as the medicinal fluid leaves the fluid source, and
   the microprocessor is configured to:
      calculate an amount of medicinal fluid that has been dispensed and an actual flow rate based on the weight of the fluid source detected over a period of time,
      perform a comparison of the actual flow rate with a set flow rate,
      adjust a volume and a flow rate delivered by a delivery mechanism of the IV infusion system based on the comparison, and
      adjust a period of time for delivery of the medicinal fluid to compensate for the volume and the flow rate delivered by the delivery mechanism.

2. The measurement device according to claim 1, wherein the fluid source is configured to hang from the weight sensing mechanism.

3. The measurement device according to claim 1, wherein the weight sensing mechanism is equipped with an accelerometer.

4. The measurement device according to claim 1, wherein the weight sensor is a strain gauge.

5. The measurement device according to claim 1, wherein the weight sensor is a weight scale.

6. The measurement device according to claim 1, wherein the weight sensing mechanism is fixed to an IV pole.

7. The measurement device according to claim 1, wherein the weight sensing mechanism further comprises a display.

8. The measurement device according to claim 7, wherein the display is configured to depict an actual volume and the actual flow rate of the IV infusion system.

9. A measurement system for IV pump infusion, comprising:
   a fluid source configured to store medicinal fluid;
   a weight sensing mechanism configured to sense a weight of the fluid source;
   a microprocessor communicatively coupled with the weight sensing mechanism, the microprocessor configured to calculate a change in the sensed weight over a period of time, calculate an actual flow rate based on the change in the sensed weight, and compare the actual flow rate to a set flow rate;
   an IV tubing connected to the fluid source;
   a delivery mechanism configured to deliver the medicinal fluid; and
   a communication unit communicatively coupled with the microprocessor and the delivery mechanism, the communication unit configured to communicate between the microprocessor and the delivery mechanism;
   wherein the communication unit is configured to transmit the calculated change in weight and the actual flow rate in real time to the delivery mechanism and adjust a volume and a flow rate delivered by the delivery mechanism based on the sensed weight, and
   wherein the microprocessor is further configured to adjust a period of time for medicine delivery to compensate for the volume and the flow rate delivered by the delivery mechanism.

10. The measurement system according to claim 9, wherein the delivery mechanism comprises:
    an IV pump configured to move the medicinal fluid through the IV tubing, and
    a drive unit communicatively coupled to the communication unit and configured to operate the IV pump.

11. The measurement system according to claim 9, wherein the communication unit further comprises:
    an input device configured to receive a set IV pump rotational speed and an infusion flow rate, and an activation input to begin an infusion process, and
    a memory configured to store measurement data and calculations.

12. The measurement system according to claim 9, wherein the fluid source is configured to hang from the weight sensing mechanism.

13. The measurement system according to claim 9 wherein the weight sensing mechanism is fixed to an IV pole.

14. The measurement system according to claim 9, wherein the weight sensing mechanism comprises:
    a weight sensor.

15. The measurement system according to claim 14, wherein the microprocessor is communicatively coupled to the communication unit and is configured to transmit the calculated flow rate to an IV infusion system for regulation of the infusion.

16. A method of measuring a flow rate and a volume of a fluid in an IV pump infusion system, comprising the steps of:
    coupling a weight sensing mechanism to a fluid source of the IV pump infusion system, wherein the fluid source contains a medicinal fluid;
    priming the IV pump infusion system with a saline solution;
    inputting a set rotational speed and a set flow rate for a peristaltic IV pump into a processor of the IV pump infusion system;
    administering the medicinal fluid out of the fluid source and into an infusion system;
    measuring a change in mass over a time interval of the fluid source containing medicinal fluid by the weight sensing mechanism during administration;

monitoring an accelerometer to verify that the fluid source is stable;

calculating an actual flow rate and an actual volume of the medicinal fluid inside the infusion system by the processor, based on the change in mass measured over the time interval;

displaying the actual flow rate and an actual volume of the medicinal fluid on an internal display;

communicating the measured change in mass and the time interval to the peristaltic IV pump;

adjusting a rotational speed, a volume, and a flow rate of the peristaltic IV pump based on the actual volume and the actual flow rate; and adjusting a period of time for infusion to compensate for the rotational speed, the volume, and the flow rate of the IV peristaltic pump.

17. The method according to claim 16, further comprising coupling the fluid source directly to the weight sensing mechanism.

18. The method according to claim 16 wherein said coupling further comprises fixing the weight sensing mechanism onto an IV pole.

* * * * *